United States Patent [19]

Rizkalla

[11] 4,335,059

[45] Jun. 15, 1982

[54] PREPARATION OF CARBOXYLIC ACID ANHYDRIDES

[75] Inventor: Nabil Rizkalla, River Vale, N.J.

[73] Assignee: Halcon Research and Development Corp., New York, N.Y.

[21] Appl. No.: 219,788

[22] Filed: Dec. 24, 1980

[51] Int. Cl.$^{3}$ ...................... C07C 51/56; C07C 51/54; C07C 53/12

[52] U.S. Cl. .................................... 260/549; 260/546

[58] Field of Search ................................ 260/549, 546

[56] References Cited

U.S. PATENT DOCUMENTS 4,002,678 1/1977 Naglieri et al. .................... 260/549

4,115,444 9/1978 Rizkalla .............................. 260/549

*Primary Examiner*—Natalie Trousof

*Assistant Examiner*—Frederick W. Pepper

*Attorney, Agent, or Firm*—William C. Long; Riggs T. Stewart; Harold N. Wells

[57] ABSTRACT

A carboxylic acid anhydride, such as acetic anhydride, is prepared from a carboxylate ester or a hydrocarbyl ether in carbonylation processes comprising the use of an iodide, carbon monoxide and a molybdenum-nickel or tungsten-nickel component in the presence of a promoter comprising an organo-phosphorus compound or an organo-nitrogen compound wherein the phosphorus and nitrogen are trivalent.

4 Claims, No Drawings

PREPARATION OF CARBOXYLIC ACID ANHYDRIDES

This invention relates to the preparation of anhydrides of carboxylic acids, more particularly mono-carboxylic acids, and especially the anhydrides of lower alkanolic acids, such as acetic anhydride, by carbonylation.

Acetic anhydride has been known as an industrial chemical for many years and large amounts are used in the manufacture of cellulose acetate. It has commonly been produced on an industrial scale by the reaction of ketene and acetic acid. It is also known that acetic anhydride can be produced by the decomposition of ethylidene diacetate, as well as by the oxidation of acetaldehyde, for example. Each of these "classic" processes has well-known drawbacks and disadvantages and the search for an improved process for the production of acetic anhydride has been a continuing one. Proposals for producing anhydrides by the action of carbon monoxide upon various reactants (carbonylation) have been described, for example, in Reppe et al U.S. Pat. Nos. 2,729,561, 2,730,546, and 2,789,137. However, such prior proposals involving cobalt or nickel catalysts have required the use of very high pressures. In later patents, carbonylation at lower pressures has been proposed but only as a route to the preparation of acetic acid. French Pat. No. 1,573,130, for example, describes the carbonylation of methanol and mixtures of methanol with methyl acetate in the presence of compounds of Group VIII noble metals such as iridium, platinum, palladium, osmium and ruthenium and in the presence of bromine or iodine under more moderate pressures than those contemplated by Reppe et al. Similarly, South African Pat. No. 68/2174 produces acetic acid from the same reactants using a rhodium component with bromine or iodine. Schultz (U.S. Pat. Nos. 3,689,533 and 3,717,670) has disclosed a vapor-phase process for acetic acid production employing various catalysts comprising a rhodium component dispersed on a carrier. None of these later carbonylation disclosures, however, refers to or contemplates the preparation of acetic anhydride or other carboxylic acid anhydrides.

Most recently, improved processes for preparing carboxylic acid anhydrides, including acetic anhydride, have been disclosed in British Pat. No. 1,468,940 and in U.S. Pat. No. 4,115,444. In all of these recent processes, however, a Group VIII noble metal is an essential catalyst component. Consequently, while entirely effective, these processes suffer from the need to employ expensive, relatively rare metals.

U.S. Pat. No. 4,002,678 discloses the use of a non-noble metal system involving a promoted nickel-chromium catalyst. While effective, this catalyst system is not completely satisfactory from the standpoint of reaction rate.

It is an object of the present invention to provide an improved process for the manufacture of carboxylic acid anhydrides, especially lower alkanoic anhydrides, such as acetic anhydride, which requires neither high pressures nor Group VIII noble metals.

In accordance with the invention, carbonylation of a carboxylic ester and/or a hydrocarbyl ether is carried out by using a molybdenum-nickel or a tungsten-nickel co-catalyst in the presence of a promoter comprising an organ-phosphorus compound or an organo-nitrogen compound wherein the phosphorus and nitrogen are trivalent, and in the presence of an iodide. The surprising discovery has been made that this co-catalyst in combination with the promoter-iodide system of the character indicated makes possible carbonylation of esters and ethers not only at relatively low pressures but with rapid, high yield production of carboxylic acid anhydrides.

Thus, in accordance with the invention, carbon monoxide is reacted with a carboxylate ester, especially a lower alkyl alkanoate, or a hydrocarbyl ether such as a lower alkyl ether, to produce a carboxylic anhydride, such as a lower alkanoic anhydride, the carbonylation taking place in the presence of an iodide e.g., a hyrdocarbyl iodide, especially a lower alkyl iodide, such as methyl iodide. Thus, acetic anhydride, for example, can be effectively prepared in a representative case by subjecting methyl acetate or dimethyl ether to carbonylation in the presence of methyl iodide. In all cases, the carbonylation is carried out under anhydrous conditions in the presence of the co-catalyst promoter-system described above. Moreover, an ester-ether mixture can be carbonylated if desired.

It will be understood that the iodine moiety does not have to be added to the system as a hydrocarbyl iodide but may be supplied as another organic iodide or as the hydroiodide or other inorganic iodide, e.g., a salt, such as the alkali metal or other metal salt, or even as elemental iodine. Following the reaction the organic components of the reaction mixture are readily separated from one another, as by fractional distillation.

In like manner, other lower alkanoic anhydrides, i.e., anhydrides of lower alkanoic acids, such as propionic anhydride, butyric anhydrides, and valeric anhydrides, can be produced by carbonylating the corresponding lower alkyl alkanoate or a lower alkyl ether. Similarly, other carboxylic acid anhydrides, e.g., the anhydrides of other alkanoic acids, such as those containing up to 12 carbon atoms, for example capric anhydrides, caprylic anhydrides and lauric anhydrides, and like higher anhydrides are produced by carbonylating the corresponding ester, e.g., alkyl akanoates containing up to 11 carbon atoms in the alkyl group and up to 12 carbon atoms in the carboxylate group, or aryl esters, or the corresponding ether, such as heptyl caprylate, nonyl decanoate, undecyl laurate, phenyl benzoate, heptyl ether, nonyl ether, phenyl ether, and the like.

It is preferred that the reactants be selected so that the resulting anhydride will be a symmetrical anhydride, i.e., having two identical acyl groups, viz., wherein R in equations (1) and (2) is the same in each instance, but it is within the scope of the invention to produce non-symmetrical or mixed anhydrides and this can be readily effected by using different combinations of reactants, e.g., by using compounds having different R groups in the foregoing reactions, as will be obvious to persons skilled in the art.

The above-described reactions can be expressed as follows:

$$CO+RCOOR \rightarrow (RCO)_2O \quad (1)$$

$$2CO+ROR \rightarrow (RCO)_2O \quad (2)$$

wherein R is a hydrocarbyl radical which may be saturated, e.g., alkyl of 1 to 11 carbon atoms, or monocyclic aryl, e.g., phenyl or aralkyl, e.g., benzyl. Preferably, R is lower alkyl i.e., an alkyl group of 1 to 4 carbon atoms, such as methyl, ethyl, n-propyl, i-propyl, n-butyl, sec-butyl and t-butyl.

The hydrocarbyl radical may be substituted with substituents which are inert in the reactions of the invention.

The more volatile components such as alkyl iodide and unreacted ether or ester in the final product mixture can be readily removed, as by distillation, for recycling, and the net yield of product is substantially exclusively the desired carboxylic anhydride. In the case of liquid-phase reaction which is preferred, the organic compounds are easily separated from the metal-containing components, as by distillation. The reaction is suitably carried out in a reaction zone to which the carbon monoxide, the ester or ether, the iodide, the specified co-catalyst and the promoter are fed. No water is produced in the abovedescribed reactions and anhydrous or substantially anhydrous conditions are employed.

In carrying out the process of the invention, a wide range of temperatures, e.g., 25° to 350° C. are suitable but temperatures of 100° to 250° C. are preferably employed and the more preferred temperatures generally lie in the range of 125° to 225° C. Temperatures lower than those mentioned can be used but they tend to lead to reduced reaction rates, and higher temperatures may also be employed but there is no particular advantage in their use. The time of reaction is also not a parameter of the process and depends largely upon the temperature employed, but typical residence times, by way of example, will generally fall in the range of 0.1 to 20 hours. The reaction is carried out under super-atmospheric pressure but, as previously mentioned, it is a feature of the invention that excessively high pressures, which require special high-pressure equipment, are not necessary. In general, the reaction is effectively carried out by employing a carbon monoxide partial pressure which is preferably 15 to 2000 psi and most preferably 30 to 1200 psi, although carbon monoxide partial pressures of 1 to 10,000 psi can also be employed. By establishing the partial pressure of carbon monoxide at the values specified, adequate amounts of this reactant are always present. The total pressure is, of course, that which will provide the desired carbon monoxide partial pressure and preferably it is that required to maintain the liquid phase and in this case the reaction can be advantageously carried out in an autoclave or similar apparatus. The final reaction mixture will normally contain volatile components such as a hydrocarbyl iodide, unreacted ester or ether along with the product anhydride and these volatile components, after separation from the anhydride, can be recycled to the reaction. At the end of the desired residence time the reaction mixture is separated into its several constituents, as by distillation. Preferably, the reaction product is introduced into a distillation zone which may be a fractional distillation column, or a series of columns, effective to separate the volatile components from the product anhydride and to separate the product anhydride from the less volatile catalyst and promoter components of the reaction mixture. The boiling points of the volatile components are sufficiently far apart that their separation by conventional distillation presents no particular problem. Likewise, the higher boiling organic components can be readily distilled away from the metal co-catalyst components and any organic promoter which may be in the form of a relatively non-volatile complex. The co-catalyst components, and promoter can then be combined with fresh amounts of ester or ether and carbon monoxide and reacted to produce additional quantities of anhydride.

The process is advantageously carried out in the presence of a solvent or diluent, particularly when the reactant has a relatively low boiling point, as in the case of dimethyl ether. The presence of a higher boiling solvent or diluent, which may be the product anhydride itself, e.g., acetic anhydride in the case of dimethyl ether, or which may be the corresponding ester, e.g., methyl acetate, again in the case of methyl ether, will make it possible to employ more moderate total pressure. Alternatively, the solvent or diluent may be any organic solvent which is inert in the environment of the process such as hydrocarbons, e.g., octane, benzene, toluene, or carboxylic acids, e.g., acetic acid, and the like. The carboxylic acid, when used, should preferably correspond to the anhydride being produced. A solvent or diluent is suitably selected which has a boiling point sufficiently different from the desired product in the reaction mixture so that it can be readily separated, as will be apparent to persons skilled in the art.

The carbon monoxide is preferably employed in substantially pure form, as available commercially, but inert diluents such as carbon dioxide, nitrogen methane, and noble gases can be present if desired. The presence of inert diluents does not effect the carbonylation reaction but their presence makes it necessary to increase the total pressure in order to maintain the desired CO partial pressure. The carbon monoxide, like other reactants should, however, be essentially dry, i.e., the CO and the other reactants should be reasonably free from water. The presence of minor amounts of water such as may be found in the commercial forms of the reactants is, however, entirely acceptable. It is preferable that the amount of moisture be kept to a minimum since the presence of water has been found to have an adverse effect upon the activity of the co-catalyst promoter system. Hydrogen which may be present as an impurity is not objectionable and even may tend to stabilize the catalyst. Indeed, in order to obtain low CO partial pressures the CO fed may be diluted with hydrogen or any inert gas such as those above mentioned.

The co-catalyst components can be employed in any convenient form, viz., in the zero valent state or in any higher valent form. For example, the nickel and the molybdenum or tungsten can be the metals themselves in finely divided form, or a compound, both organic or inorganic, which is effective to introduce the co-catalyst components into the reaction system. Thus, typical compounds include the carbonate, oxide, hydroxide, bromide, iodide, chloride, oxyhalide, hydride, lower alkoxide (methoxide), phenoxide, or molybdenum, tungsten or nickel carboxylates wherein the carboxylate ion is derived from an alkanoic acid of 1 to 20 carbon atoms such as acetates, butyrates, decanoates, laurates, benzoates, and the like. Similarly, complexes of any of the co-catalyst components can be employed, e.g., carbonyls and metal alkyls as well as chelates, association compounds and enol salts. Examples of other complexes include bis-(triphenylphosphine) nickel dicarbonyl, tricyclopentadienyl trinickel dicarbonyl, tetrakis (triphenylphosphite) nickel, and corresponding complexes of the other components, such as molybdenum hexacarbonyl and tungsten hexacarbonyl.

Included among the catalyst component listed above are complexes of the metal co-catalyst component with organic promoter ligands derived from the organic promoters hereinafter described. Particularly preferred are the elemental forms, compounds which are iodides, and organic salts, e.g., salts of the monocarboxylic acid corresponding to the anhydride being produced. It will be understood that the foregoing compounds and complexes are merely illustrative of suitable forms of the several co-catalyst components and are not intended to be limiting.

The specified co-catalyst components employed may contain impurities normally associated with the commercially available metal or metal compounds and need not be purified any further.

The organo-phosphorus promoter is preferably a phosphine, e.g., a phosphine of the formula

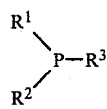

wherein $R^1$, $R^2$ and $R^3$ may be same or different, and are alkyl, cycloalkyl, aryl groups, amide groups or halogen atoms, preferably containing up to 1 to 20 carbon atoms in the case of alkyl and cycloalkyl groups and 6 to 18 carbon atoms in the case of aryl groups. Typical phosphines include trimethylphosphine, tripropylphosphine, tricyclohexylphosphine and triphenylphosphine.

Preferably the organo-nitrogen promoter is a tertiary amine or a polyfunctional nitrogen-containing compound, such as an amide, a hydroxy amine, a keto amine, a di-, tri and other polyamine or a nitrogen-containing compound which comprises two or more other functional groups. Typical organo-nitrogen promoters include 2-hydroxypyridine, 8-quinolinol, 1-methylpyrrolidinone, 2-imidazolidone, N,N-dimethylacetamide, dicyclohexylacetamide, dicyclohexyl-methylamine, 2,6-diaminopyridine, 2-quinolinol, N,N-diethyltoluamide, and imidazole.

Although generally the organic promoters are added separately to the catalyst system, it is also possible to add them as complexes with the co-catalyst metals such as bis(triphenylphosphine) nickel dicarbonyl, and tetrakis (triphenyl phosphite) nickel. Both free organic promoters and complexed promoters can also be used. Indeed, when a complex of the organic promoter and the nickel and/or co-catalyst components are used, free organic promoter can also be added as well.

The amount of each co-catalyst component is in no way critical and is not a parameter of the process of the invention and can vary over a wide range. As is well known to persons skilled in the art, the amount of catalyst used is that which will provide the desired suitable and reasonable reaction rate since reaction rate is influenced by the amount of catalyst. However, essentially any amount of catalyst will facilitate the basic reaction and can be considered a catalytically-effective quantity. Typically, however, each component of the co-catalyst is employed in the amount of 1 mol per 10 to 10,000 mols of ester or ether, preferably 1 mol per 100 to 5,000 mols of ester or ether, and most preferably 1 mol per 500 to 1,000 mols of ester or ether.

The ratio of nickel to its co-catalyst component can vary. Typically, it is one mol of nickel per 0.01 to 100 mols of the other co-catalyst component, preferably the nickel component is used in the amount of 1 mol per 0.1 to 20 mols, most preferably 1 mol per 1 to 10 mols of the other co-catalyst component.

The quantity of organic promoter can also vary widely but typically it is used in the amount of 1 mol per 0.1 to 10 mols of co-catalyst components, preferably 1 mol per 0.5 to 5 mol, most preferably 1 mol per 1 to 5 mols of co-catalyst components.

As previously mentioned, in the working up of the reaction mixtures, e.g., by distillation, the promoter components can be readily recovered and recycled to the reaction. The nickel and co-catalyst metal generally remain as the least volatile components, and are recycled or otherwise handled together. They may, however, distill with the volatile components, e.g., in the case of nickel carbonyl. The same is true of the promoter components.

When an ether is used as the reactant, the corresponding ester is formed as an intermediate, e.g., methyl acetate is formed when dimethyl ether is carbonylated in accordance with the invention. The intermediate ester may be recovered from the reaction mixture, if desired, e.g., by fractional distillation, for example during the separation of the volatile components of the reaction mixture as described above.

The amount of iodide component may also vary widely but, in general, it should be present in an amount of at least 10 mols (expressed as I) per hundred mols of ester or ether. Typically, there are used 10 to 50 mols of the iodide per 100 mols of ester or ether, preferably 17 to 35 mols per 100 mols. Ordinarily, more than 200 mols of iodide per 100 mols of ester or ether are not used.

It will be apparent that the above-described reactions lend themselves readily to continuous operation in which the reactants and catalyst, preferably in combination with the promoter, are continuously supplied to the appropriate reaction zone and the reaction mixture continuously distilled to separate the volatile organic constituents and to provide the desired product or products, e.g., carboxylic acid anhydride, with the other organic components being recycled and, in the case of liquid-phase reaction, a residual nickel co-catalyst-containing (and promoter-containing) fraction also being recycled.

A particular embodiment of the catalyst comprising the molybdenum-nickel or tungsten-nickel co-catalyst component, the organic promoter component and the iodide component can be represented by the following formula X:T:Z:Q, wherein X is molybdenum or tungsten, T is nickel, X and T being in zero valent form or in the form of a halide, an oxide, a carboxylate of 1 to 20 carbon atoms, a carbonyl or an hydride; Z is an iodide source which is hydrogen iodide, iodine, an alkyl iodide wherein the alkyl group contains 1 to 20 carbon atoms or an alkali metal iodide, and Q is an organo-phosphorus compound or an organo-nitrogen compound wherein the phosphorus and the nitrogen are trivalent. Preferred are the nitrogen and phosphorus compounds previously indicated as being preferably used and in the most preferred form Q is a phosphine of the formula

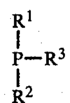

as hereinbefore defined, especially hydrocarbyl phosphines, the molar ratio of X to T being 0.1–10:1, the molar ratio of X+T to Q being 0.05–20:1 and the molar ratio of Z to X+T being 1–1,000:1.

It will also be apparent that the catalytic reaction involved in the process of the invention can be carried out in the vapor phase, if desired, by appropriate control of the total pressure in relation to the temperature so that the reactants are in vapor form when in contact with the catalyst. In the case of vapor-phase operation, and in the case of liquid-phase operation, if desired, catalyst components may be supported i.e., they may be dispersed on a carrier of conventional type such as alumina, silica, silicon carbide, zirconia, carbon, bauxite, attapulgus clay, and the like. The catalyst components can be applied to the carriers in conventional manner, e.g., by impregnation of the carrier with a solution of the catalyst component. Concentrations upon the carrier may vary widely, e.g., 0.01 weight percent to 10 weight percent, or higher. Typical operating conditions for vapor-phase operation are a temperature of 100° to 350° C., preferably 150° to 275° C. and most perferably 175° to 255° C., a pressure of 1 to 5,000 p.s.i.a., preferably 59 to 1,500 p.s.i.a. and most preferably 150 to 500 p.s.i.a., with space velocities of 50 to 10,000 $hr.^{-1}$, preferably 200 to 6,000 $hr.^{-1}$ and most preferably 500 to 4,000 $hr.^{-1}$ (STP). In the case of a supported catalyst, the iodide component is included with the reactants and not on the support.

The following examples will serve to provide a fuller understanding of the invention, but is it to be understood that they are given for illustrative purposes only, and are not to be construed as limitative of the invention. In the examples, all parts are on a molar basis and all percentages are by weight, unless otherwise indicated. The various reactants and catalyst components are charged to the reaction vessel which is then closed and brought to the reaction temperature indicated.

EXAMPLE 1

A magnetically-stirred Hastelloy Parr bomb is employed as the reaction vessel. The bomb is charged with methyl acetate (250 parts), methyl iodide (250 parts), bis-triphenylphosphine nickel dicarbonyl (8 parts) plus molybdenum carbonyl (15 parts) as co-catalyst, and triphenyl phosphine (25 parts), is swept out with argon and is pressured to 600 psig with carbon monoxide. The vessel is heated to 200° C. with stirring during which time the pressure rises to about 1,200 psig. The temperature is maintained at 180° C. and the pressure is maintained at 1,200 psig by recharging with carbon monoxide when needed. After 4 hours reaction time, G. C. analysis of the reaction product shows it to be composed of 30 mol % methyl acetate and 70 mol % acetic anhydride.

EXAMPLE 2

Example 1 is repeated except that the original gas charge contains 5% hydrogen and 95% CO. Subsequent recharges of gas are made with pure carbon monoxide. After 1.75 hours reaction time, G. C. analysis of the reaction product shows it to be composed of 18 mol % methyl acetate and 82 mol % acetic anhydride.

EXAMPLE 3

Example 1 is again repeated with the exception that the temperature is 160° C. After 3 hours of reaction time, G. C. analysis of the reaction product shows it to be composed of 45 mol % methyl acetate and 55 mol % acetic anhydride.

EXAMPLE 4

Example 1 is repeated once again except that the bistriphenylphosphine nickel dicarbonyl is replaced with nickel acetate. After 6 hours of reaction time, G. C. analysis of the reaction product shows it to contain 22 mol % methyl acetate and 75 mol % acetic anhydride.

EXAMPLE 5

When Example 1 is repeated again, except that the bistriphenylphosphine nickel dicarbonyl is replaced with nickel iodide, after 5 hours of reaction time, G. C. analysis of the reaction product shows it to contain 18 mol % methyl acetate and 81 mol % acetic anhydride.

EXAMPLE 6

Again repeating Example 1 but with the molybdenum carbonyl being replaced with molybdenum acetate, after 5 hours of reaction time, G. C. analysis of the reaction product shows it to contain 20 mol % methyl acetate and 78 mol % acetic anhydride.

EXAMPLE 7

Example 1 is repeated with the exception that molybdenum hexacarbonyl is replaced with an equivalent quantity of tungsten hexacarbonyl. The reaction product, after a reaction time of 8 hours, corresponds to that described in Example 1.

EXAMPLE 8

A reactor as described in Example 1 is charged with 250 parts methyl acetate, 250 parts methyl iodide, 15 parts triphenylphosphine, 7 parts bis-triphenylphosphine nickel dicarbonyl and 5 parts molybdenum hexacarbonyl. The reactor is pressured with 100 psig of hydrogen and up to 600 psig with carbon monoxide and is then heated to 185° C. with stirring. The pressure is adjusted to 1,200 psig with carbon monoxide and is kept at that level by recharging carbon monoxide when needed. After 4 hours of reaction time, G. C. analysis shows that the reaction product to conain 70 mol % acetic anhydride.

EXAMPLE 9

Example 8 is repeated with the exception that molybdenum carbonyl is replaced with an equal weight of chromium carbonyl. After 4 hours of reaction time, G. C. analysis shows that the reaction product contains only 39.6 mol % acetic anhydride.

EXAMPLE 10

A pressure reactor as described in Example 1 is charged with 250 g. methyl iodide, 250 g. methyl acetate, 25 g. imidazole, 10 g. nickel iodide, 10 g. molybdenum hexacarbonyl. The reactor is pressured with 200 psig hydrogen and then to 600 psig carbon monoxide. The reactor is heated up to 180° C. with stirring. The pressure increases to 950 psig and is maintained at that pressure by recharging carbon monoxide when needed. After 4 hours reaction time, G. C. analysis of the reaction mixture shows that it contains 42 mol % acetic anhydride.

What is claimed is:

1. A process for the preparation of carboxylic acid anhydrides which comprises reacting a carboxylate ester and/or a hydrocarbyl ether with carbon monoxide in the presence of a catalytically-effective quantity of a molybdenum-nickel or tungsten nickel co-catalyst component, in the presence of an iodide and in the presence of a promoter comprising an organo-phosphorus compound or an organo-nitrogen compound wherein the phosphorus and nitrogen are trivalent.

2. A process as defined in claim 1, wherein the cocatalyst component comprises molybdenum-nickel.

3. A process as defined in claim 1, wherein the promoter is a phosphine.

4. A process as defined in claim 3, wherein the cocatalyst promoter comprises molybdenum-nickel and the promoter is a phosphine.

* * * * *